United States Patent
Dacanay

(10) Patent No.: US 11,819,641 B2
(45) Date of Patent: Nov. 21, 2023

(54) VASCULAR ACCESS DEVICES WITH INTEGRATED SAFETY FEATURES

(71) Applicant: Rhodel G. Dacanay, Poway, CA (US)

(72) Inventor: Rhodel G. Dacanay, Poway, CA (US)

(73) Assignee: Rhodel G. Dacanay, Poway, CA (US)

( * ) Notice: Subject to any disclaimer, the term of this patent is extended or adjusted under 35 U.S.C. 154(b) by 856 days.

(21) Appl. No.: 16/557,505

(22) Filed: Aug. 30, 2019

(65) Prior Publication Data

US 2020/0360669 A1 Nov. 19, 2020

Related U.S. Application Data

(60) Provisional application No. 62/848,878, filed on May 16, 2019.

(51) Int. Cl.
 *A61M 25/09* (2006.01)

(52) U.S. Cl.
 CPC ......... *A61M 25/09041* (2013.01); *A61M 2025/09125* (2013.01); *A61M 2025/09133* (2013.01); *A61M 2205/0238* (2013.01); *A61M 2205/582* (2013.01); *A61M 2205/583* (2013.01)

(58) Field of Classification Search
 CPC ......... A61M 2025/09125; A61M 2025/09133; A61M 25/09041; A61M 2025/09058; A61M 2025/09116; A61M 2025/09175; A61M 2205/0238; A61M 2205/582; A61M 2205/583; A61M 2025/0008; A61M 25/0075; A61M 25/0169; A61M 25/0172; A61M 25/09; A61M 2025/0076; A61M 2025/0079
 See application file for complete search history.

(56) References Cited

U.S. PATENT DOCUMENTS

| | | | |
|---|---|---|---|
| 5,304,156 A | 4/1994 | Sylvanowicz et al. | |
| 5,350,399 A | 9/1994 | Erlebacher et al. | |
| 5,497,782 A | 3/1996 | Fugoso | |
| 5,634,475 A | 6/1997 | Wolvek | |
| 6,752,800 B1 | 6/2004 | Winston et al. | |
| 2003/0097138 A1 | 5/2003 | Reydel | |
| 2007/0161969 A1 | 7/2007 | Andersen | |
| 2007/0255217 A1* | 11/2007 | Burkett | B29C 48/12 604/164.13 |
| 2008/0194994 A1* | 8/2008 | Bown | A61M 25/09 148/559 |
| 2008/0300574 A1 | 12/2008 | Belson et al. | |
| 2009/0162531 A1* | 6/2009 | Nesbitt | A61L 29/18 427/2.12 |
| 2012/0065622 A1* | 3/2012 | Cornish | A61M 25/09 604/528 |

(Continued)

OTHER PUBLICATIONS

International Preliminary Report on Patentability in corresponding International Application No. PCT/US2019/049159 dated Nov. 25, 2021 (10 pages).

(Continued)

*Primary Examiner* — Tiffany Leggette
*Assistant Examiner* — Leah J Swanson
(74) *Attorney, Agent, or Firm* — William A. Hector; Venable LLP

(57) ABSTRACT

Removable vascular access devices include integrated safety features configured to prevent unintended migration of guidewires into a patient's body. The guidewires include safety guidewires that provide a tactile and/or visual indicator of insertion length. Introducer sets include the removable vascular access devices, catheters and the guidewires.

13 Claims, 7 Drawing Sheets

(56) References Cited

U.S. PATENT DOCUMENTS

| | | | |
|---|---|---|---|
| 2013/0030416 A1 | 1/2013 | Fernandes et al. | |
| 2013/0282036 A1* | 10/2013 | Schaeffer | A61M 25/09 606/159 |
| 2014/0018732 A1* | 1/2014 | Bagaoisan | A61M 25/0136 604/95.04 |
| 2014/0194822 A1* | 7/2014 | Wu | A61B 17/3417 604/171 |
| 2018/0014899 A1* | 1/2018 | Kuroda | A61M 25/09 |
| 2021/0016059 A1* | 1/2021 | Brown | A61M 25/0606 |

OTHER PUBLICATIONS

PCT/US2019/049159 International Search Report and Written Opinion dated Dec. 13, 2019.

McGee et al. "Preventing Complications of Central Venous Catherization." The New England Journal of Medicine, Mar. 20, 2003, 348(12):1123-1133.

Vannucci et al. "Retained Guidewires After Intraoperative Placement of Central Venous Catheters." Anesthesia Analgesia, Jul. 2013, 117(1):102-108.

Indian first Examination Report in corresponding Indian Patent Application No. 202117058023 dated Jul. 17, 2023 (8 pages).

Extended European Search Report in corresponding European Application No. 19928635.2 dated May 22, 2023 (7 pages).

Tamara L. Williams, MSN, RN; T. Andrew Bowdle, MD, PhD, Fase; Bradford D. Winters, MD, PhD; Stephen D.Pavkovic, JD, MPH, RN; Marilyn K. Szekendi, PhD, RN; "Guidewires Unintentionally Retained During Central Venous Catheterization"; Journal of the Association for Vascular Access (2014) 19 (1): 29-34; < https://doi.org/10.1016/j.java.2013.12.001>; 7 pages.

* cited by examiner

VASCULAR ACCESS DEVICES WITH INTEGRATED SAFETY FEATURES

CROSS REFERENCE TO RELATED APPLICATION

This application claims the benefit of priority under 35 U.S.C. § 119(e) of U.S. Ser. No. 62/848,878, filed May 16, 2019, the entire content of which is incorporated herein by reference.

BACKGROUND OF THE INVENTION

Field of the Invention

The invention relates generally to vascular access devices and more specifically to vascular access devices having integrated safety features configured to prevent unintended migration of guidewires into a patient's body.

Background Information

Over 5 million central venous catheters are inserted every year in the United States alone (N ENGL J MED 2003; 348:1123-33, McGee, D C, Gould, M K. Preventing Complications of Central Venous Catheterization). An over-the-wire or Seldinger Technique is standard for such procedures. However, this technique is associated with guidewire retention at a rate of approximately 1:3,291 procedures (ANAES ANALG 2013; 117:102-8, Vanucci, A, Jeffcoat, A, Ifune, C, Salinas, C, Duncan, J R, Wall, M. Retained Guidewires after Intraoperative Placement of Central Venous Catheters). Guidewire retention can cause arrhythmias, thrombosis, cardiac perforation, cardiac tamponade, and death. (J ASSOC VASC ACCESS 2014; 19:29-34, Williams, T L, Bowdle, A T, Winters, B D, Pavkovic, S D, Skekendi, M K). Guidewires Unintentionally Retained During Central Venous Catheterization). Thus, a need exists for a reliable means of preventing the inadvertent retention of catheter guidewires.

SUMMARY OF THE INVENTION

The present invention relates to vascular access devices having integrated safety features configured to prevent unintended migration of guidewires into a patient's body. Accordingly, in an exemplary aspect, the invention provides an internal sheath inserted into a vascular catheter. The sheath includes an elongated body having an inner surface forming a lumen along an axis and a safety device disposed within the elongated body. The safety device may include one or more protrusions extending from the inner surface of the elongated body toward the axis thereof (e.g., towards the opposing inner wall of the internal sheath), wherein when the elongated body is inserted over a guidewire, each of the one or more protrusions applies frictional force onto the guidewire to prevent unintended migration thereof. In various embodiments, each of the one or more protrusions is in compressive contact with adjacent protrusions and/or the opposing wall of the inner sheath to close or substantially close the lumen of the elongated body. Thus, in various embodiments, each of the one or more protrusions may apply one or more of frictional, compressive, and interlocking force onto the guidewire to prevent unintended migration thereof. In various embodiments, each of the one or more protrusions may be substantially perpendicular to the axis or may be angled inward toward the axis of the elongated body. In various embodiments, each of the one or more protrusions contacts a textured coating of the guidewire, wherein frictional force increases between the one or more protrusions and the textured coating. In various embodiments, each of the one or more protrusions is disposed equidistantly along the inner surface of the elongated body. In various embodiments, each of the one or more protrusions further comprises a corresponding deformable flexure extending toward the axis of the lumen. In various embodiments, each deformable flexure comprises one or more teeth protruding therefrom, wherein each of the one or more teeth are inclined relative to the flexure. Thus, each deformable flexure engages corresponding teeth or notches of the guidewire to form a one-way mechanism similar to a "zip-tie" mechanism. In various embodiments, the one-way mechanism may be a leaflet. In various embodiments, the guidewire may include unidirectional protrusions (e.g., barbs, needles, pins, cones, etc.). In various embodiments, the guidewire may include a curved end that creates a "J" tip.

In various embodiments, the sheath may further include a luer-lock, screw, or tapered mechanism disposed at a proximal end of the elongated body. In various embodiments, the elongated body and the safety device are formed as a single unit. In various embodiments, the elongated body and the safety device are formed separately and permanently bonded to one another. In various embodiments, the safety device is integrated into a vascular access device.

In another exemplary aspect, the invention provides a safety guidewire. The safety guidewire includes a guidewire having a length and a first "J" tip disposed at a distal end thereof, and a textured coating disposed over a portion of the length of the guidewire. In various embodiments, the textured coating provides a tactile indication of insertion length and/or depth within a patient. In various embodiments, the guidewire may be colored for visual indication of insertion length and/or depth into a patient. In various embodiments, about 8-11 centimeters of the distal end of the guidewire is not coated by the textured coating. In various embodiments, the textured coating is disposed over the proximal end, wherein the textured coating is configured to increase engagement of one or more protrusions of a safety device through which the guidewire is traversed. In various embodiments, the textured coating is a polymer coating. In various embodiments, the safety guidewire may also include a second "J" tip disposed at a proximal end of the guidewire. The second "J" tip may be easily straightened by a user. In various embodiments the guidewire itself may provide a one-way mechanism via the "J" tip and/or one or more extensions disposed at a proximal end of the guidewire and extending outward from a central axis of the guidewire. In various embodiments, the guidewire may engage the protrusions of the safety sheath to create the one-way mechanism to prevent unwanted migration of the guidewire into a patient's body. In various embodiments, the extensions are disposed radially, helically, or randomly along a length of the guidewire. In various embodiments, the extensions are disposed linearly along a length of the guidewire. In various embodiments, the extensions are formed equidistant around a circumference of the guidewire. In various embodiments, each of the plurality of extensions has different length and/or thickness relative to one another.

In another exemplary aspect, the invention provides an introducer set. The introducer set includes at least a catheter, a guidewire, and the sheath described above. In various embodiments, the guidewire is the safety guidewire described above.

BRIEF DESCRIPTION OF THE DRAWINGS

Embodiments of the present invention and their advantages are best understood by referring to the detailed description that follows. It should be appreciated that like reference numerals are used to identify like elements illustrated in one or more of the figures.

DETAILED DESCRIPTION OF THE INVENTION

Figure 1A:
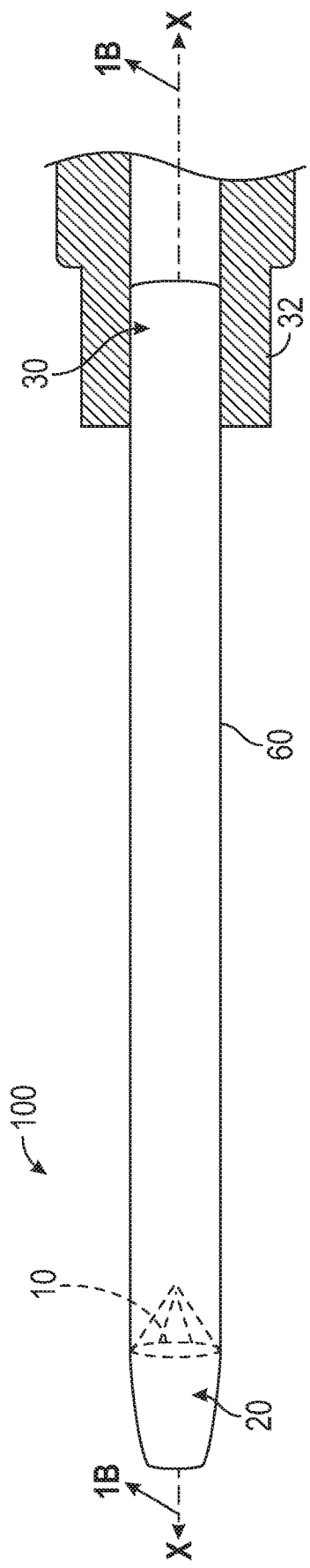
FIG. 1A is a pictorial diagram showing a side view of an exemplary safety sheath or safety catheter with an integrated safety device in accordance with one or more embodiments of the present disclosure.

The present invention relates to vascular access devices having integrated safety features configured to prevent unintended migration of guidewires into a patient's body.

Before the present invention and methods are described, it is to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Guidewires are typically used to facilitate insertion of a medical device, such as a catheter, into a body lumen, such as, for example, a blood vessel. The classic or modified Seldinger technique is a common way to deploy the medical device over the guidewire. Briefly, catheter insertion using the Seldinger technique can include one or more of the following steps: administer local anesthetic; locate vein using finder needle connected to a syringe; remove syringe once needle is appropriately situated in body lumen; confirm placement of needle (e.g., using hemodynamic monitoring such as central venous pressure, color, or absence of pulsatile blood flow, for example); advance guidewire through needle lumen into the target vessel; hold guidewire in place, remove needle; enlarge cutaneous puncture site (e.g., via a scalpel); insert dilator over the guidewire to further enlarge site; remove dilator; thread tip of catheter over the guidewire; grasp catheter near skin and advance into vein with a slight twisting motion; remove guidewire; place caps on input ports to reduce risk of air embolism; aspirate catheter ports to remove air; flush ports, e.g., with saline or heparin.

A potential life-threatening complication with the use of central venous catheters is migration of the guidewire with the intravascular fragment or migration of the entire guidewire centrally as a foreign body embolus, such as when the operator may not be fully attentive to the guidewire. It has been estimated that this complication occurs with a frequency of approximately $1/1000$-$2/1000$. Most often, an intravascular fragment of a guidewire or a complete guidewire becomes lodged within the right heart where it may produce an arrhythmia or compromise a valve. Less frequently, the intravascular guidewire lodges more distally within a pulmonary artery with the risk of causing a pulmonary infarction.

There is also a risk of undesired guidewire migration at any step where the guidewire is at least partially in the body, after the guidewire is advanced through the needle lumen into the target vessel. It is often inconvenient to necessitate a second operator to be present and "sterile" for the sole purpose of holding onto the proximal end of the guidewire for preventing unwanted guidewire migration during a catheter insertion or exchange procedure. Furthermore, other methods of preventing unwanted guidewire migration, such as clamping the proximal end of the guidewire with a hemostat to lock the guidewire in place can undesirably damage the guidewire.

While guidewires are more commonly used to cannulate a vein or an artery, other body lumens including a lymphatic vessel, biliary tree, etc., can also be cannulated and embodiments described herein can be used to prevent guidewire migration in systems and methods thereof, and for that matter, any procedure in which a guidewire is used to deliver a medical or non-medical device.

Figure 1B:
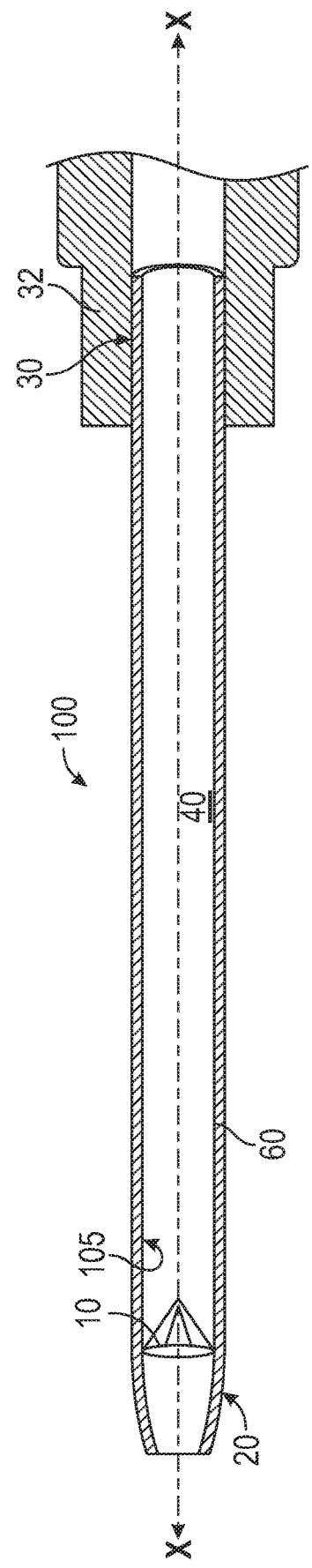
FIG. 1B is a pictorial diagram of a cross-sectional view, taken along line 1B-1B of FIG. 1A, showing the exemplary safety sheath or safety catheter with the integrated safety device in accordance with one or more embodiments of the present disclosure.

Accordingly, the present invention provides a safety feature (also referred to herein as a "safety device") for incorporation into a vascular access device (e.g., sheath or catheter). More specifically, a safety device may be integrated into a sheath of a vascular access catheter (e.g., the sheath may be a removeable inner safety sleeve of a catheter) used for accessing a lumen of a patient's body. In various embodiments, the inner safety sleeve may extend beyond the body of the catheter to also act as a dilator. Referring now to the drawings, wherein the showings are for purposes of illustrating embodiments of the present invention only and not for the purposes of limiting the same, FIGS. 1A and 1B show a side view and a cross-sectional side view (taken along line 1B-1B of FIG. 1A), respectively, of a sheath 100 with an integrated safety device 10, in accordance with one or more embodiments of the present disclosure. As shown in FIGS. 1A and 1B, the safety device 10 is disposed within a sheath 100 and includes a one-way mechanism. The sheath 100 includes an elongated body 60 having a lumen 40 defined by an inner surface 105 and extending along a longitudinal center axis X. The elongated body 60 has opposing first and second ends, such as a distal end 20 (i.e., the end of the sheath 100 that is closest to the patient during insertion of the sheath 100 over a guidewire and into a lumen of a patient's body) and a proximal end 30 (i.e., the end of sheath 100 that is farthest from the patient during insertion of sheath 100). In various embodiments, the proximal end 30 of the elongated body 60 may be formed to include a connector 32 (e.g., a conventional luer-lock, screw connector, or other suitable connectors, adapters, or hubs).

In other embodiments, the safety sheath 100 does not have a connector and must therefore be removed from an inserted catheter prior to use of the catheter. For example, the sheath 100 may be disposed inside a catheter (e.g., as an inner safety sleeve) such that the sheath 100 and catheter are simultaneously inserted over a guidewire into a lumen of a patient's body so that the sheath 100 engages the guidewire (as discussed further herein). The sheath 100 and the engaged guidewire may thereafter be removed from the catheter, and thus, removed from the lumen of the patient, leaving the catheter positioned within the lumen of the patient. The connector of the catheter may then be connected to, for example, a syringe or intravenous fluid line. In various embodiments, the safety device 10 includes a one-way mechanism and is disposed within the elongated body 60. For example, the safety device 10 may be located within the lumen 40 at the distal end 20, or within close proximity to the distal end 20, of the elongated body 60. Thus, when the sheath 100 is inserted over a guidewire (e.g., guidewire 70 as shown in FIGS. 2A-2B), the one-way mechanism of the safety device 10 engages the guidewire, thereby preventing unwanted migration of the guidewire into the patient even with minimal guidewire insertion into the sheath 100.

Figure 2A:
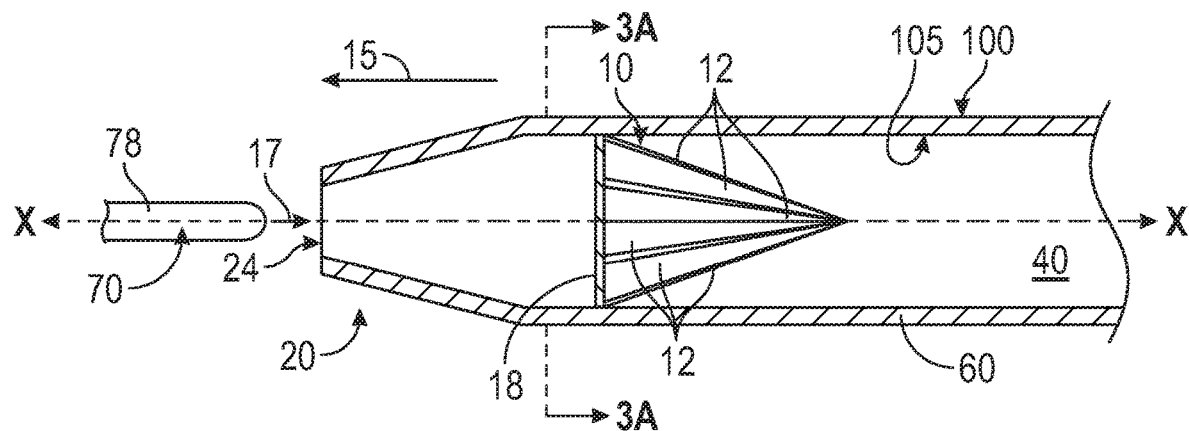
FIG. 2A is a pictorial diagram of a partial cross-sectional view, taken along line 1B-1B of FIG. 1A, showing the exemplary safety sheath or safety catheter with integrated safety device in a resting position in accordance with one or more embodiments of the present disclosure.
Figure 2B:
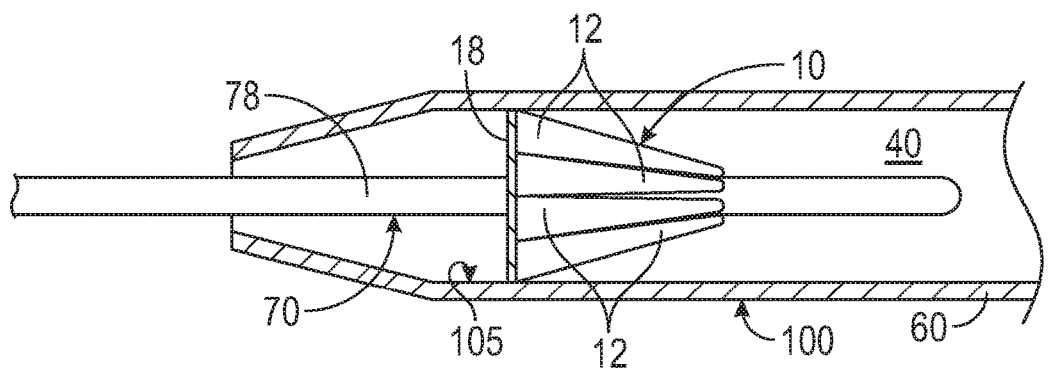
FIG. 2B is a pictorial diagram of a partial cross-sectional view, taken along line 1B-1B of FIG. 1A, showing the safety sheath or safety catheter with an exemplary integrated safety device in an engaged position in accordance with one or more embodiments of the present disclosure.

FIGS. 2A and 2B show partial cross-sectional side views of an exemplary safety device 10 in a resting position and in an engaged position, respectively, in accordance with one or more embodiments of the disclosure. In various embodiments, the safety device 10 may be conically-shaped and may include one or more protrusions 12, as discussed further herein. While the safety device 10 is shown as being disposed at the distal end 20 of the elongated body 60, it should be understood that the safety device 10 may be located anywhere within the lumen 40 of the elongated body 60, and that the one-way mechanism may be configured for compressive, frictional, and/or interlocking engagement with a guidewire 70.

As shown in FIG. 2A, the sheath 100 may be inserted over the guidewire 70, as indicated by directional arrow 15, such that at least a portion of the guidewire 70 traverses through an opening 24 of elongated body 60 and into lumen 40, for example, in a direction indicated by directional arrow 17. As shown in FIG. 2B, the safety device 10 may then engage the guidewire 70 using compressive clamping force to prevent undesirable movement of the guidewire 70 within lumen 40 of sheath 100 (e.g., in a direction opposite of direction 17) and/or within a lumen of the patient's body.

Figure 3A:
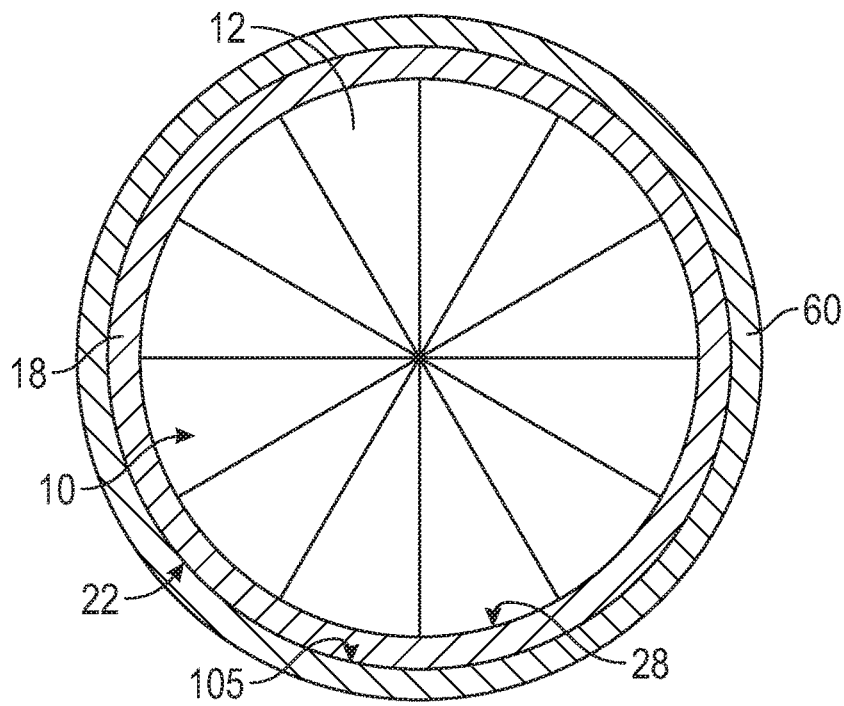
FIG. 3A is a pictorial diagram of a cross-sectional view, taken along line 3A-3A of FIG. 2A, showing the safety device closing the lumen of the safety sheath or safety catheter in accordance with one or more embodiments of the present disclosure.
Figure 3B:
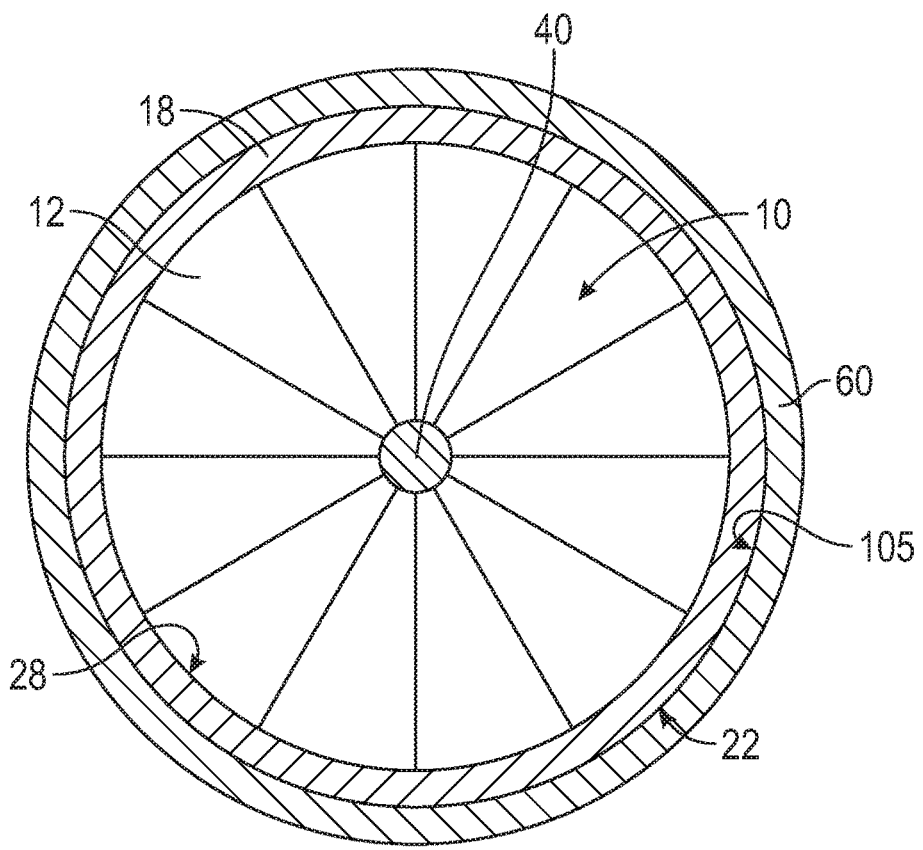
FIG. 3B is a pictorial diagram of a cross-sectional view, taken along line 3A-3A of FIG. 2A, showing an alternative embodiment of the same exemplary safety device in accordance with one or more embodiments of the present disclosure.
Figure 7:
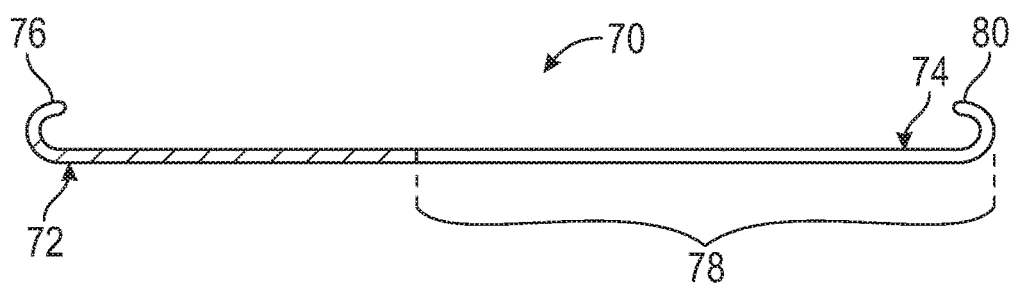
Figure 8:
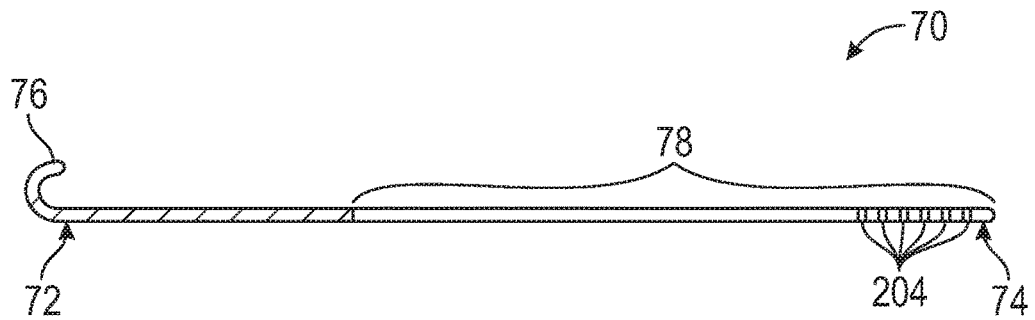
Figure 9:
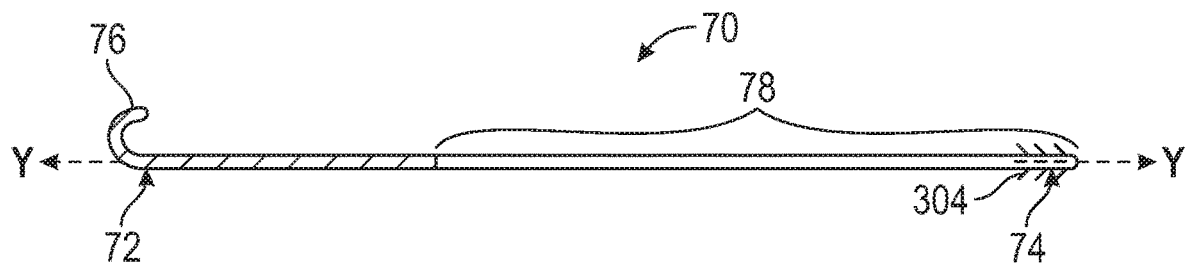

In various embodiments, the one-way mechanism of the safety device 10 may include one or more protrusions 12, each protrusion 12 extending from the inner surface 105 of the elongated body 60 of the sheath 100 toward the center axis X thereof. In embodiments where the safety device 10 is conically shaped (as shown in FIGS. 2A-3B), the protrusions 12 may be circumferentially oriented along the inner surface 105 and may extend radially toward center axis X. Referring now to FIGS. 3A and 3B, the protrusions 12 may be adjoined to an annular ring 18 of the safety device 10, which may be connected to inner surface 105, as discussed further herein. In various embodiments, each of the one or more protrusions 12 may be in compressive contact with the adjacent protrusions 12, thereby forming a closed, one-way mechanism within the lumen 40 of the sheath 100. As such, when the sheath 100 is inserted over a guidewire 70 along axis X, the protrusions 12 are urged apart from each other, resulting in application of compressive force toward axis X and onto the guidewire 70, thereby preventing unwanted guidewire migration. In various embodiments, the guidewire 70 may have a textured coating 78 (as shown in FIGS. 7-9) configured to provide a tactile and/or visual indication of insertion length and depth and/or to increase frictional force applied to guidewire 70 resulting from the compressive force applied by the one or more protrusions 12. The textured coating 78 may be formed from any substance suitable for use in medical devices, such as a polymer, provided that the coating provides a tactile and/or visual indication of insertion length or depth and/or increases the frictional force resulting from the compressive force applied by the one or more protrusions 12.

FIGS. 3A and 3B illustrate cross-sectional views, taken along line 3A-3A of FIG. 2A, showing various embodiments of safety device 10 in accordance with one or more embodiments of the present disclosure. In various embodiments, the protrusions 12 may be formed to completely close the lumen 40 (as shown in FIG. 3A) or may substantially close the lumen 40, leaving a small opening through which the guidewire 70 is inserted (as shown in FIG. 3B). In various embodiments, the protrusions 12 may be substantially perpendicular to the axis X of the sheath 100, or may be angled, for example, inward toward axis X of the elongated body 60 of the sheath 100 (as shown in FIGS. 2A and 2B). For example, each protrusion 12 may provide an inclined surface relative to axis X such that the protrusions 12 are unidirectionally oriented about axis X.

In various embodiments, the proximal end 30 of the sheath 100 will be formed with or without a typical luer-lock, screw lock, or tapered mechanism (i.e., connector 32) that allows for attachment of a syringe or intravascular fluid line. As such, when the sheath 100 is formed without a connector 32 at the proximal end 30, a user will be required to remove the sheath 100 prior to use of the catheter for the procedure. In various embodiments, the sheath 100 will extend beyond a tip of the catheter to act as dilator, thereby eliminating the need for a separate dilation step when inserted into the lumen of a patient.

It should be understood that while the safety device 10 is described as being formed integral to the internal sheath 100, the present invention also contemplates formation of the safety device 10 as a separate unit from the internal sheath 100. In such embodiments, the safety device 10 may include an annular ring 18 having an outer surface 22 and an inner surface 28, where the outer surface 22 is sized for contacting the inner surface 105 of the elongated body 60. As shown in FIGS. 3A and 3B, the one or more protrusions 12 may extend from the inner surface 28 of the annular ring 18 toward the center axis X of sheath 100. When formed as a separate unit, the annular ring 18 of safety device 10 may be permanently bonded to the inner surface 105 of the sheath 100 by any known means, followed by any known sterilization method suitable for medical or non-medical devices to be inserted into a body lumen. Alternatively, or in addition thereto, annular ring 18 may be permanently bonded to the inner surface 105 of the elongated body 60 under aseptic conditions.

In various embodiments, the safety device 10 may also be used in conjunction with a catheter to be inserted into a body lumen. For example, the safety device 10 may be incorporated into the distal end of a catheter that is directly inserted over a guidewire 70, rather than, or in addition to, incorporating the safety device 10 on the internal sheath 100.

One common type of catheter inserted over a guidewire is a central venous catheter, which is typically inserted via an internal jugular, subclavian, axillary, or femoral vein approach. A central venous catheter, such as those described, for example, in U.S. Pat. No. 6,206,849, hereby incorporated by reference in its entirety, can include one or more input ports operably connected to a conduit fluidly connected to the catheter body. The catheter may be used for hemodialysis treatment and may also be inserted in a similar fashion into the femoral vein or internal jugular vein, for example. Some non-limiting examples of dialysis catheters that can be used or modified for use herein include Mahurkar™ or Quinton™ catheters, or tunneled catheters such as Hickman™ or Groshong™ catheters.

As provided herein, the invention may, in action, serve some purposes that are also served by a dilator; however, the invention, in an exemplary form is not intended to be inserted into a patient and then removed prior to the insertion of the vascular access device. Rather the invention may extend beyond the distal end of the catheter to be inserted in order to accomplish the function of a separate dilator, including facilitating the insertion of an otherwise flimsy catheter into a patient lumen, thereby eliminating the need for a separate dilation step.

Figure 4A:
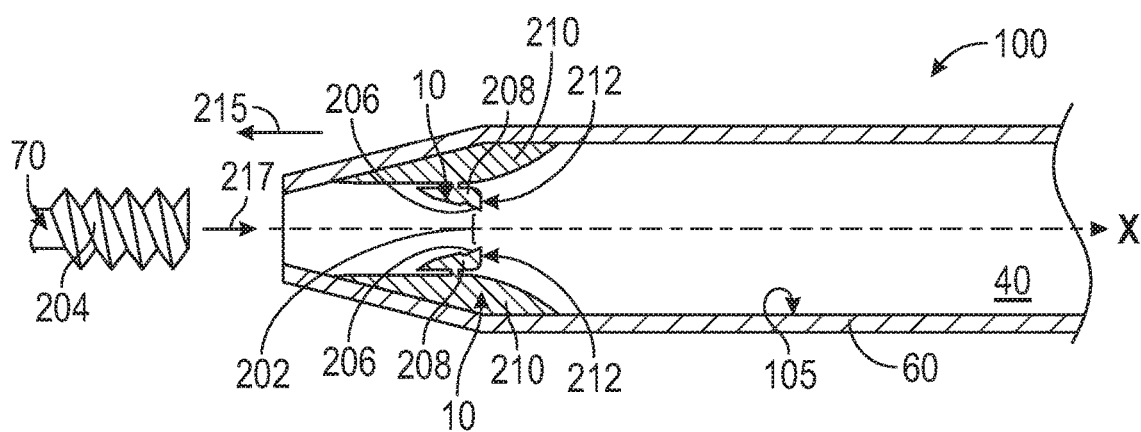
FIGS. 4A and 4B are pictorial diagrams showing various views of an exemplary safety sheath with an alternative exemplary embodiment of the safety device and corresponding guidewire in accordance with one or more embodiments of the present disclosure.
Figure 4B:
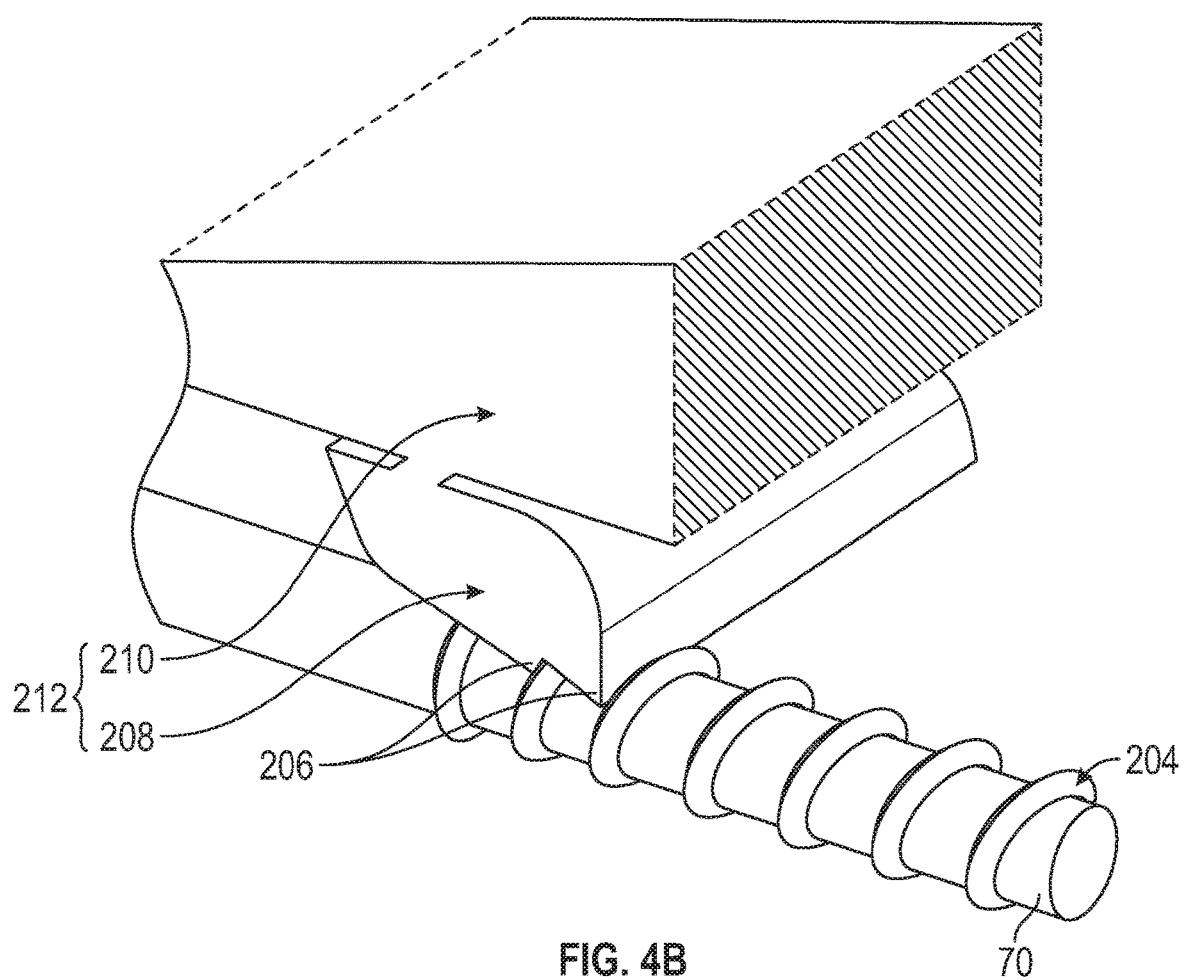

Referring now to FIGS. 4A and 4B, an alternative exemplary embodiment of safety device 10 is provided in accordance with the disclosure. As shown, the safety device 10 may include one or more protrusions, such as engagement members 212, configured for one-way engagement of the guidewire 70 (e.g., similar to a ratcheting "zip-tie" mechanism). In various embodiments, the safety device 10 may include one engagement member 212 (as shown in FIG. 4B) or may include two opposing engagement members 212 (as shown in FIG. 4A). In various embodiments, safety device 10 may include four, five, six or more protrusions disposed equidistantly along the entirety of the periphery of the inner surface 105 of the elongated body 60, and spaced equidistantly from one another about axis X. In various embodiments, each of the engagement members 212 may include a corresponding deformable flexure 208 extending toward axis X of the elongated body 60. In various embodiments, each of the engagement members 212 may be directly attached to the inner surface 105 of the elongated body 60 or may be formed on a base 210, which is bonded to the inner surface 105 of the elongated body 60. In one or more embodiments, each flexure 208 may have one or more teeth 206 protruding therefrom that are inclined relative to the surrounding, adjoining surface of the flexure 208.

As such, when guidewire 70 traverses through the lumen 40 and through a channel 202 defined by the flexures 208 of the safety device 10, the safety device 10 may be configured for ratcheted engagement (i.e., similar to a "zip-tie" mechanism) with the guidewire 70 in that at least a portion of each flexure 208 may translate outward (i.e., away from axis X and toward the inner surface 105 of the sheath 100). As described above, the teeth 206 protrude from the flexures 208 and extend unidirectionally from each flexure 208 at an angle so that the guidewire 70 may readily traverse through the safety device 10 in a first direction (e.g., direction 217) when the sheath 100 is inserted over the guidewire 70 (e.g., in direction 215). Thus, teeth 206 are configured to engage and prevent movement of the guidewire 70 in a second direction (e.g., a direction opposite of direction 217). In various embodiments, teeth 206 are configured to engage the guidewire 70 using an applied longitudinal force and/or compressive contact, as described above. In various embodiments, the guidewire 70 may have a textured coating 78 configured to increase frictional force applied by the teeth 206 onto guidewire 70. In another exemplary configuration, guidewire 70 may include complementary circumferential surfaces, such as corresponding threading 204 or recessed notches, that are configured to engage the teeth 206 of the safety device 10. When so configured, the engagement of teeth 206 of the safety device 10 with corresponding threading 204 or notches of the guidewire prevent movement of the guidewire in the second direction (i.e., the direction opposite of direction 217).

Figure 5A:
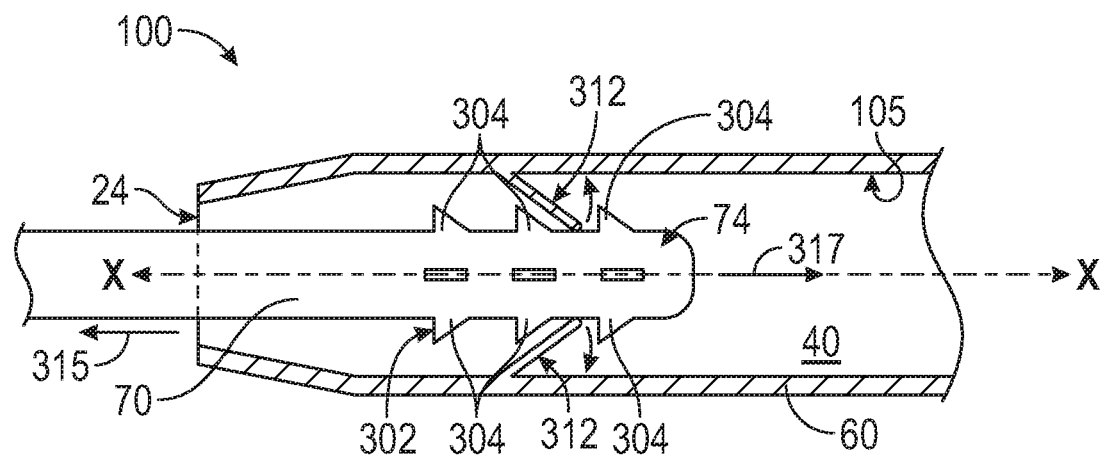
FIGS. 5A and 5B are pictorial diagrams showing various views of an exemplary safety sleeve with an alternative exemplary embodiment of a safety device in accordance with one or more embodiments of the present disclosure.
Figure 5B:
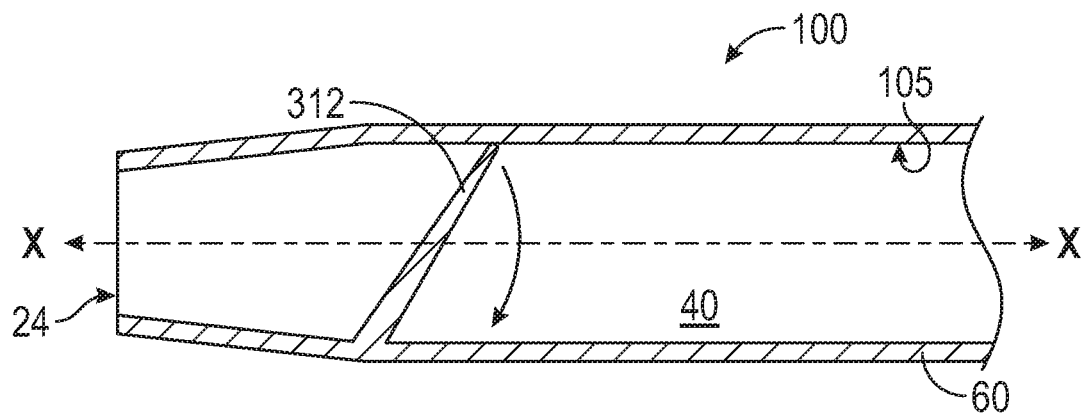

Referring now to FIGS. 5A and 5B, alternative exemplary embodiments of safety device 10 are provided in accordance with the disclosure. As shown, the safety mechanism 10 may include one or more protrusions, such as tabs 312, formed to resemble circular leaflets (e.g., leaflets that close the lumen 40) and/or blade-like structures. For example, as shown in FIG. 5B, the safety device 10 may provide one tab 312 (e.g., a circular leaflet) that is bonded to the inner surface 105 of elongated body 60, where the tab 312 creates a plane that is angled relative to axis X, thereby closing or substantially closing the lumen 40 of sheath 100. Upon insertion of the sheath 100 over guidewire 70 (causing guidewire 70 to be inserted into lumen 40 and through safety device 10), tab 312 flexes toward the adjoining inner surface 105 (as indicated by the curved arrow). In various embodiments, the safety device 10 may include a plurality of tabs 312, similar to protrusions 12, as shown in FIG. 5A. Thus, tabs 312 may be configured to flex and translate outward (i.e., away from axis X) upon insertion of the sheath 100 over the guidewire 70 (as indicated by the arcuate arrows in FIGS. 5A and 5B). For example, sheath 100 may be inserted over the guidewire 70 in a direction indicated by arrow 315, and the guidewire 70 may traverse through the lumen 40 and safety device 10 in a direction indicated by arrow 317 such that tabs 312 may each bend or translate away from axis X and toward their respective adjoining inner surfaces 105 of body 60.

As shown in FIGS. 6-9, the invention also provides a guidewire 70 for reducing the risk of inadvertent passage of the guidewire 70 into the patient and/or insertion beyond a predetermined distance in accordance with one or more embodiments of the present disclosure. As is known in the art, the approximate distance from the sternal angle to the right atrium of the adult human heart is 8-11 centimeters. Thus, medical personnel typically avoid inserting a guidewire more than about 7.5 centimeters to prevent damage to the surrounding organs or vessels. However, a user must also ensure that an adequate length of the guidewire extends outside of the patient for use in inserting the catheter. As such, medical personnel typically leave a length that is at least about 10 centimeters longer than the vascular catheter that is to be inserted to ensure proper use thereof.

Accordingly, as briefly discussed above, the present invention provides a guidewire 70 having disposed thereon a textured coating 78 on a portion of its length. The textured coating 78 may thus provide a user with a tactile indicator of sufficient insertion length into the patient and thus prevent over-insertion thereof. In various embodiments, the textured coating 78 may be color-coded to provide a visual indicator of insertion length in addition to the tactile indicator. The textured coating 78 may be formed from any substance suitable for use in medical devices, such as a polymer, provided that the texture is sufficient for use as a tactile indicator of insertion length. In various embodiments, the textured coating 78 may provide additional engagement force with the one or more protrusions 12, flexures 208, or tabs 312 of the safety device 10 described above.

Figure 6:
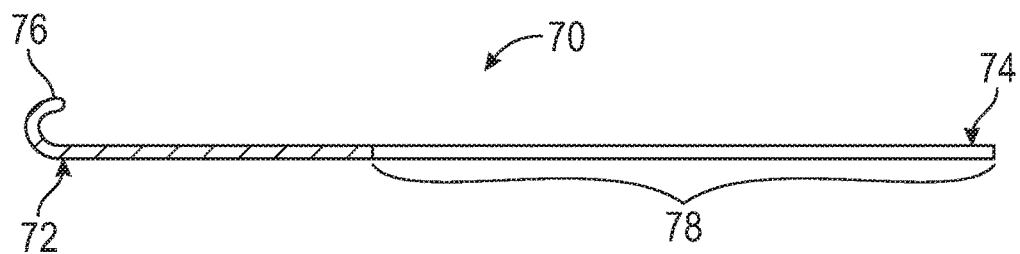
FIGS. 6-9 are pictorial diagrams showing side views of exemplary guidewires in accordance with one or more embodiments of the present disclosure.

As is known in the art, guidewires 70 are available in movable and fixed core configurations, are typically formed from stainless steel, and may include a "J" tip disposed at an end thereof. Guidewires may also be coated with a polymer coating, such as polytetrafluoroethylene (PTFE) to provide a smooth, slick surface for insertion into a body lumen. As shown in FIG. 6, the guidewire 70 has a "J" tip 76 disposed at the distal end 72 configured to avoid puncture of surrounding organs or vessels. In various embodiments, the guidewire 70 of the present invention may further include a second, easily straightened, "J" tip 80 disposed at the proximal end 74 thereof to further prevent over-insertion of the guidewire 70 into the patient (FIG. 7). In various embodiments, the "J" tip 80 may additionally provide frictional force within the safety sheath 100 or even a standard catheter lumen in order to prevent the unintended migration of the guidewire 70 into a patient.

As shown in FIGS. 4A, 4B and 8, the guidewire 70 may include threading 204 or notches disposed at least at the proximal end 74 thereof. In various embodiments, the threading 204 is configured for ratcheting or frictional engagement with complementary surfaces (e.g., protrusions 12, teeth 206 or tabs 312) of the safety device 10 to prevent the guidewire 70 from moving in an undesired direction and/or an undesired distance within the lumen 40 of the sheath 100 (as shown, for example, in FIGS. 4A and 4B).

As shown in FIG. 9, guidewire 70 may include one or more extensions 304 (e.g., barbs) that extend from at least the proximal end 74 thereof. Each of the one or more extensions 304 may be angled such that the guidewire 70 may readily traverse in one direction (e.g., direction indicated by arrow 317 of FIG. 5A) through the lumen 40, but cannot traverse in an opposing direction (e.g., a direction opposite of direction 317) beyond a predetermined point. Once the guidewire 70 is inserted through the safety device 10 of sheath 100, extensions 304 may abut and/or engage one or more of the surfaces 302 of the tabs 312 (as shown in FIG. 5A) to prevent the guidewire 70 from moving in an unwanted direction within the sheath 100. Thus, tabs 312 may provide a lateral force and/or compressive force to prevent undesired movement of the guidewire 70 within the sheath 100, or a standard catheter, and a patient's body.

In various embodiments, the extensions 304 may be barbs, pins, cones, etc. In various embodiments, the extensions 304 are oriented unidirectionally relative to each other. In various embodiments, each of the one or more extensions 304 may have different lengths and/or thicknesses. In various embodiments, the one or more extensions 304 may be uniformly sized and shaped. In various embodiments, the extensions 304 may be positioned linearly along a length of guidewire 70. In various embodiments, multiple linear arrangements of extensions 304 may be provided on opposing sides of the guidewire 70. In various embodiments, multiple linear arrangements of extensions 304 may be provided equidistantly and/or randomly around the circumference of guidewire 70 at the proximal end 74 thereof relative to a longitudinal center axis Y thereof. In various embodiments, the extensions 304 may be positioned radially, helically, randomly, and/or positioned in any other various arrangements about at least a portion of the length of the guidewire 70. As should be understood by one skilled in the art, while certain embodiments of the safety device 10 are described as being used in conjunction with specific embodiments of the guidewire 70, the various embodiments of each may be used alone or in combination with each other while still maintaining the scope of the invention.

Figure 10:
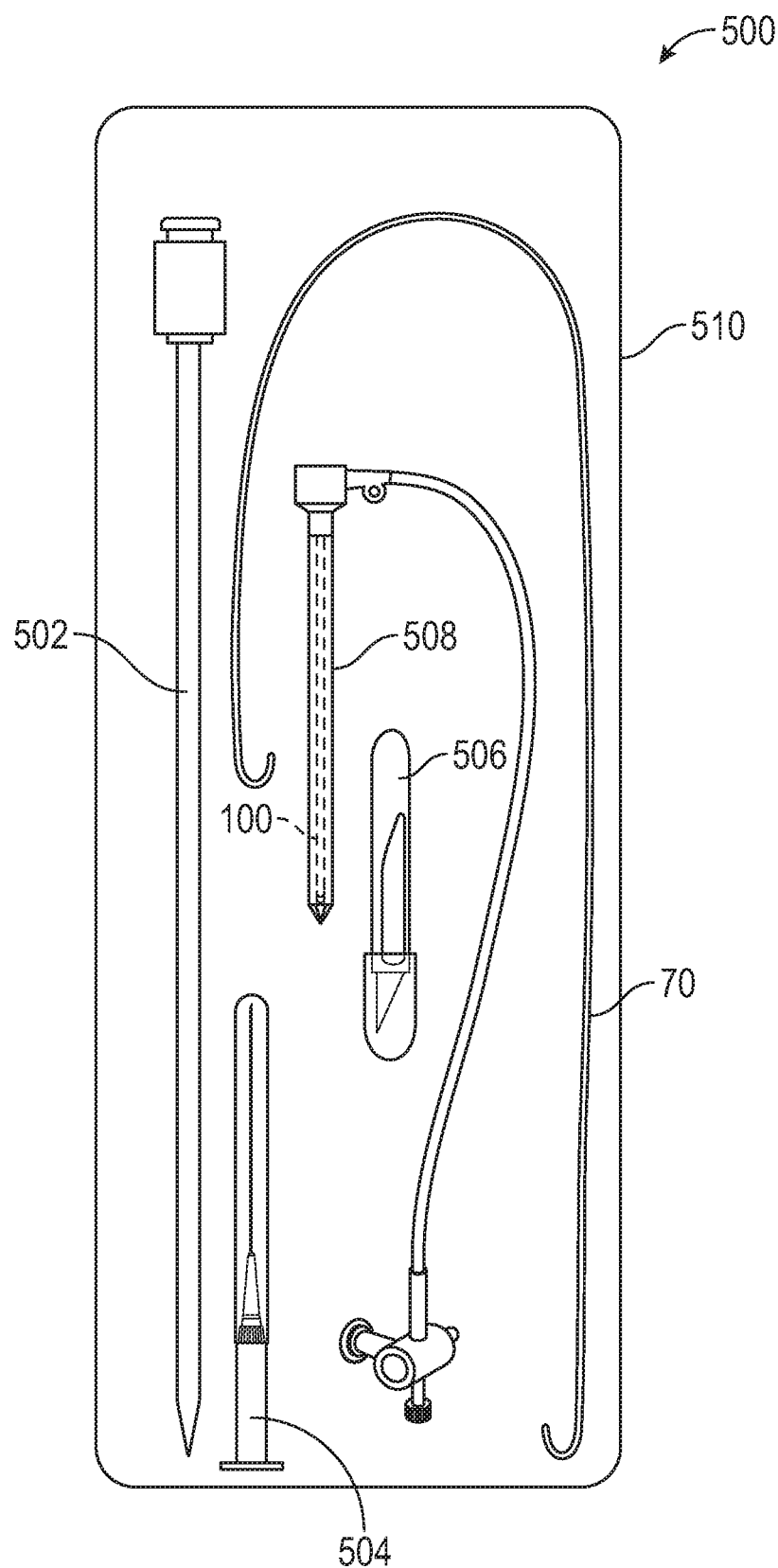
FIG. 10 is a pictorial diagram showing an exemplary introducer set in accordance with one or more embodiments of the present disclosure.

As shown in FIG. 10, the invention also provides an introducer set 500 incorporating the safety device and/or guidewire described herein. Thus, in various embodiments, the introducer set 500 may include a sheath 100 and guidewire 70 in accordance with one or more embodiments of the disclosure. In various embodiments, the introducer set 500 may be contained in a sterilized, peel-open package 510 intended for one-time use. As can be appreciated, the introducer set 500 may include various components used by physicians and/or medical technicians in, for example, diagnostic and interventional techniques (e.g., techniques known in the art that may be used for placement of vascular access devices). In various embodiments, the introducer set 500 may include a sheath 100 preloaded within an insertable catheter 508 that has, for example, an integral sidearm and corresponding adaptor, valve, and/or stopcock), the guidewire 70, a vessel dilator 502 (e.g., a dilator with a luer-lock collar), a needle 504, a scalpel 506, and/or a syringe (not shown).

In various embodiments, the introducer set 500 may include: a catheter; a safety guidewire (e.g., guidewire 70); and/or a safety sheath (e.g., sheath 100). As described above, the guidewire 70 may have a length and a first "J" tip 76 disposed at a distal end 72 thereof and one or more extensions 304 disposed at a proximal end 74 thereof. In various embodiments, the safety sheath may include an elongated body 100 having an inner surface 105 forming a lumen 40 along an axis X and a safety device 10 disposed anywhere within the elongated body 100. As described above, the safety device 10 may include one or more protrusions 12, flexures 208, or tabs 312 extending from the inner surface 105 of the elongated body 100 toward the axis X thereof or extending toward the opposing wall thereof. In use, as the elongated body 100 is inserted over the guidewire 70 and into a lumen of the patient, each of the one or more protrusions 12, flexures 208, or tabs 312 of the safety device 10 engage the one or more extensions 304 of the safety guidewire 70, thereby preventing unintended migration of the guidewire.

Although the invention has been described with reference to the above disclosure, it will be understood that modifications and variations are encompassed within the spirit and scope of the invention. Accordingly, the invention is limited only by the following claims.

What is claimed is:

1. A safety sheath for removable insertion into a vascular access catheter, the safety sheath comprising:
    (a) an elongated body having an inner surface forming a lumen along an axis; and
    (b) a safety device disposed within the elongated body, the safety device comprising one or more protrusions extending from the inner surface of the elongated body toward the axis or an opposing inner surface of the elongated body,
    wherein each of the one or more protrusions:
        applies one or more of a one-way frictional, compressive, and interlocking force onto a guidewire to prevent unintended migration of the guidewire into a patient, and
        is in compressive contact with the inner surface to substantially close the lumen of the elongated body; and
    wherein the safety sheath is configured to be removed from the catheter prior to a use of the catheter.

2. The safety sheath of claim 1, wherein each of the one or more protrusions is in compressive contact with the inner surface forming a closed, one-way mechanism.

3. The safety sheath of claim 1, wherein each of the one or more protrusions is angled inward toward the axis or the opposing inner surface of the elongated body.

4. The safety sheath of claim 1, wherein each of the one or more protrusions contacts a textured coating of the guidewire, wherein a frictional force increases between each of the one or more protrusions and the textured coating.

5. The safety sheath of claim 1, wherein each of the one or more protrusions is disposed equidistantly along the inner surface of the elongated body.

6. The safety sheath of claim 5, wherein each of the one or more protrusions further comprises a corresponding deformable flexure extending toward the axis of the lumen.

7. The safety sheath of claim 1, wherein the elongated body and the safety device are formed as a single unit.

8. The safety sheath of claim 1, wherein the elongated body and the safety device are formed separately and permanently bonded to one another.

9. An introducer set comprising: the catheter, the guidewire, and the safety sheath as set forth in claim 1.

10. The introducer set of claim 9, wherein the guidewire comprises:
    (a) the guidewire having a length and a first "J" tip disposed at a distal end of the guidewire; and
    (b) a safety coating disposed over a portion of the length of the guidewire, wherein the safety coating is disposed over a proximal end of the guidewire and is configured to increase engagement of the one or more protrusions of a the safety sheath in one direction to prevent the unintended migration of the guidewire into a the patient, and the safety sheath is configured for removable insertion into a the vascular access catheter.

11. The safety sheath of claim 1, wherein the safety sheath is configured without a connector at a proximal end, such that the safety sheath must be removed from the catheter prior to the use of the catheter.

12. An introducer set comprising:
    (a) a catheter;
    (b) a safety guidewire, wherein the safety guidewire comprises a guidewire having a length and a first "J" tip disposed at a distal end of the guidewire; and
    (c) a safety sheath, wherein the sheath comprises:
        (i) an elongated body having an inner surface forming a lumen along an axis; and
        (ii) a safety device disposed within the elongated body, the safety device comprising one or more protrusions extending from the inner surface of the elongated body toward the axis of the elongated body;
    wherein, each of the one or more protrustions:
        applies one or more of a one-way frictional, compressive, and interlocking force onto the guidewire to prevent unintended migration of the guidewire into a patient, and is in compressive contact with the inner surface to substantially close the lumen of the elongated body; and
    wherein the safety sheathis configured to be removed from the catheter prior to a use of the catheter.

13. The introducer set of claim 12, wherein the safety sheath is configured without a connector at a proximal end, such that the safety sheath must be removed from the catheter prior to the use of the catheter.

* * * * *